(12) United States Patent
Dalton

(10) Patent No.: US 7,150,726 B2
(45) Date of Patent: Dec. 19, 2006

(54) DEVICE FOR SUBCUTANEOUS INFUSION OF FLUIDS

(75) Inventor: Michael J. Dalton, Skokie, IL (US)

(73) Assignee: Norfolk Medical, Skokie, IL (US)

(*) Notice: Subject to any disclaimer, the term of this patent is extended or adjusted under 35 U.S.C. 154(b) by 77 days.

(21) Appl. No.: 10/763,510

(22) Filed: Jan. 23, 2004

(65) Prior Publication Data

US 2005/0165359 A1    Jul. 28, 2005

(51) Int. Cl.
*A61M 5/00*    (2006.01)

(52) U.S. Cl. .................................... 604/173
(58) Field of Classification Search ........... 604/171, 604/172, 173, 174, 175, 177, 180
See application file for complete search history.

(56) References Cited

U.S. PATENT DOCUMENTS

| | | | | |
|---|---|---|---|---|
| 4,051,842 A | * | 10/1977 | Hazel et al. ............... | 600/391 |
| 4,129,128 A | | 12/1978 | McFarlane | |
| 4,136,692 A | * | 1/1979 | Goldowsky ............... | 604/251 |
| 4,235,234 A | * | 11/1980 | Whitney et al. ........... | 604/117 |
| 4,362,156 A | | 12/1982 | Feller, Jr. et al. | |
| 4,380,234 A | | 4/1983 | Kamen | |
| 4,710,176 A | | 12/1987 | Quick | |
| 4,886,499 A | * | 12/1989 | Cirelli et al. ............. | 604/131 |
| 5,176,662 A | | 1/1993 | Bartholomew et al. | |
| 5,257,980 A | | 11/1993 | Van Antwerp et al. | |
| 5,533,972 A | * | 7/1996 | Gyory et al. .............. | 604/20 |
| 5,584,813 A | | 12/1996 | Livingston et al. | |
| 5,697,901 A | * | 12/1997 | Eriksson .................. | 604/46 |
| 5,858,005 A | | 1/1999 | Kriesel | |
| 6,254,586 B1 | | 7/2001 | Mann et al. | |
| 6,302,870 B1 | * | 10/2001 | Jacobsen et al. .......... | 604/272 |
| 6,334,856 B1 | * | 1/2002 | Allen et al. ............... | 604/191 |
| 6,428,515 B1 | * | 8/2002 | Bierman et al. ........... | 604/174 |
| 6,572,586 B1 | | 6/2003 | Wojcik | |
| 6,629,949 B1 | * | 10/2003 | Douglas ................... | 604/46 |
| 6,689,100 B1 | * | 2/2004 | Connelly et al. .......... | 604/117 |
| 6,808,506 B1 | * | 10/2004 | Lastovich et al. ......... | 604/47 |
| 6,908,453 B1 | * | 6/2005 | Fleming et al. ........... | 604/173 |

* cited by examiner

*Primary Examiner*—Manuel Mendez
(74) *Attorney, Agent, or Firm*—Cardinal Law Group

(57) ABSTRACT

The invention provides a subcutaneous infusion device including a delivery tube having a central lumen and a closed first end and an open second end. The device further includes a support base attached adjacent a first end of the delivery tube; and a plurality of needles extending substantially perpendicular to the support base and in communication with the central lumen of the delivery tube. A method for hydrating a patient in accordance with the invention includes pressing a support base against a skin surface of the patient and inserting a plurality of needles into a subcutaneous skin layer responsive to the pressing. The method further includes delivering a saline fluid to the subcutaneous skin layer through the needles via a delivery tube.

20 Claims, 5 Drawing Sheets

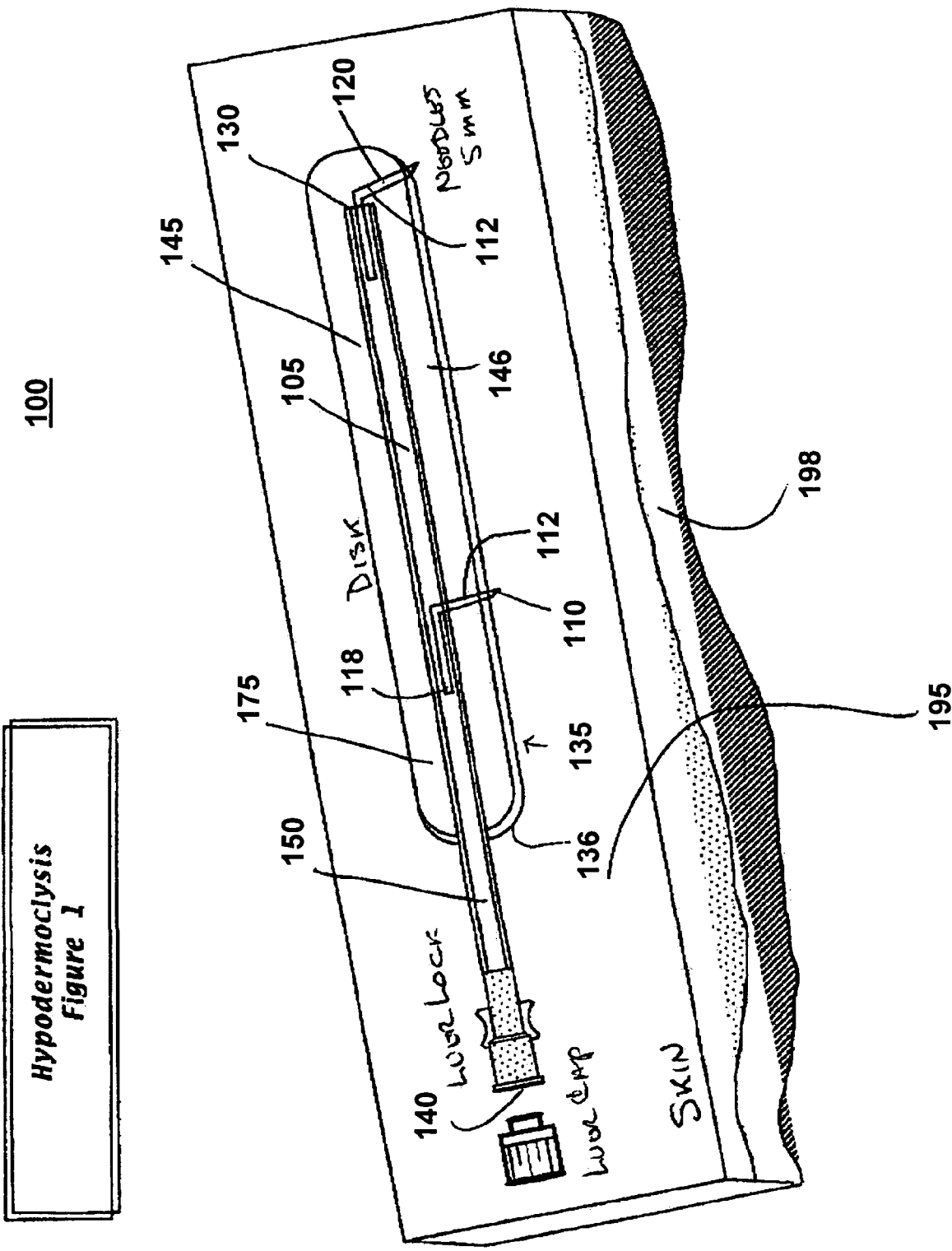
*Hypodermoclysis Figure 1*

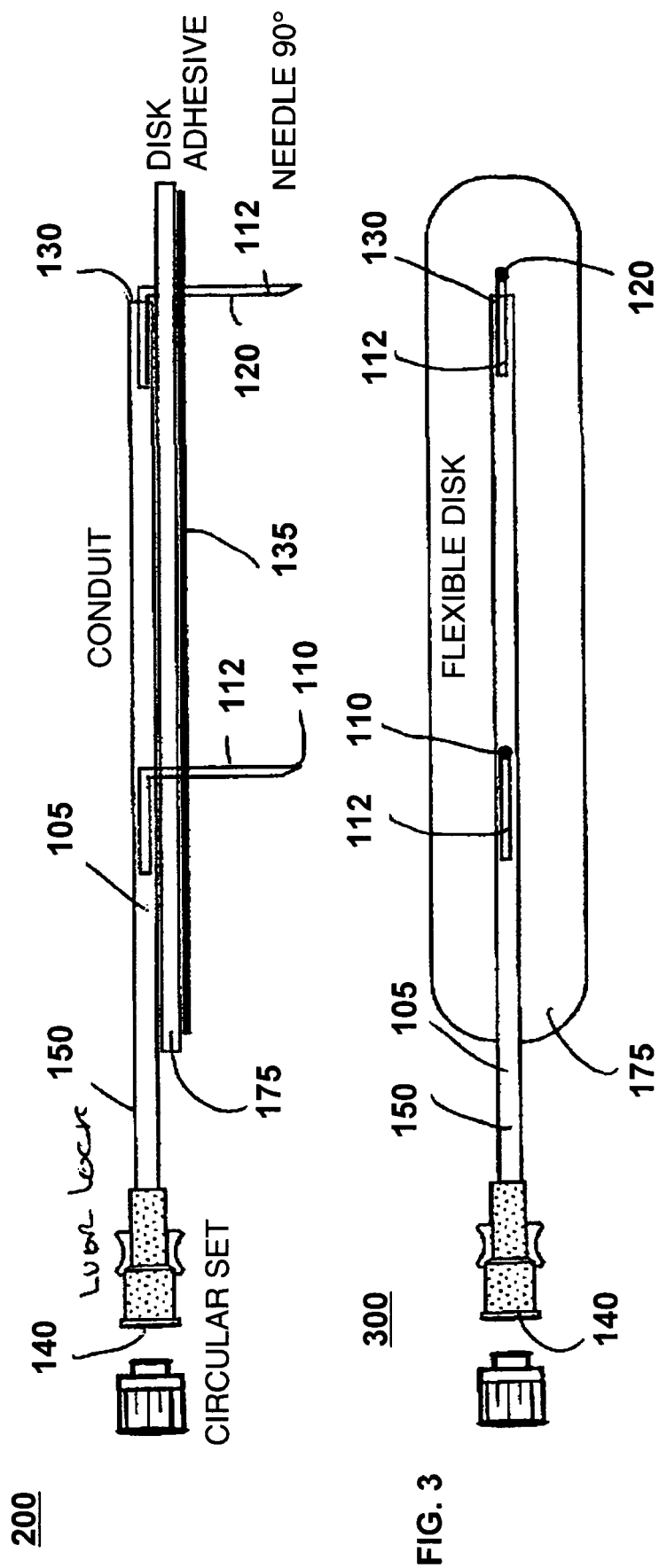

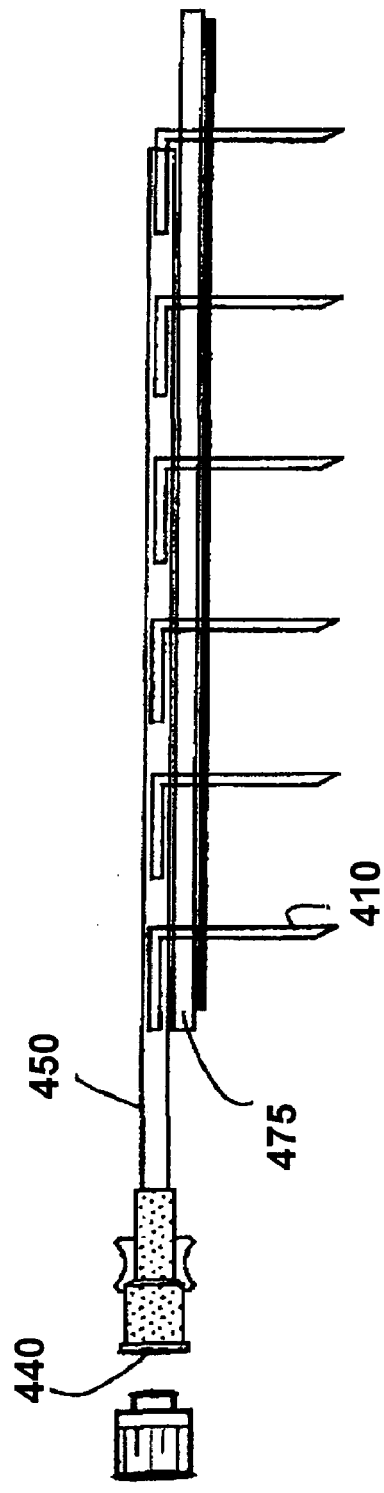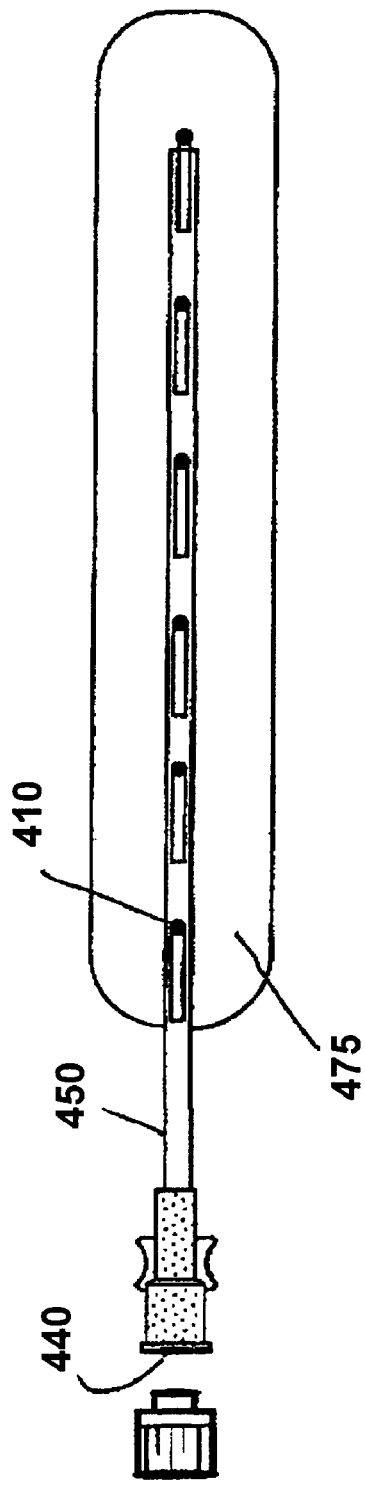

TRIANGULAR SET

CIRCULAR SET

FIG. 8 *800*
810 – Press support base against skin surface of a patient
820 – Insert plurality of needles into subcutaneous skin layer responsive to the pressing
830 – Deliver fluid to subcutaneous skin layer

DEVICE FOR SUBCUTANEOUS INFUSION OF FLUIDS

TECHNICAL FIELD

The technical field of this disclosure is medical devices, particularly for hydrating patients.

BACKGROUND OF THE INVENTION

Hypodermoclysis is a method of providing fluids to a patient that does not involve use of the intravenous or oral approaches. While often contraindicated for patients in severe dehydration, hypodermoclysis may be beneficial for palliative care, and may further be beneficial to a geriatric population. Hypodermoclysis is, in certain circumstances, less invasive than intravenous methods, and performance requires less skill than intravenous hydration.

One possible disadvantage of hypodermoclysis is the fluid flow rates possible. Because fluids do not disperse subcutaneously as quickly as in the vasculature, insertion sites are known to exhibit side effects including "camel humps" formed by fluid accumulation at the insertion site if the dispersion rate of the fluid in the subcutaneous tissue is less than the flow rate into the subcutaneous space. Thus, for a dehydrated patient, the hydration effects of hypodermoclysis treatment may be delayed as compared to intravenous treatment but the long-term results may be similar.

A variety of devices for non-intravenous hydration and therapeutic substance administration have been proposed. Wojcik, in U.S. Pat. No. 6,572,586 discloses a low profile infusion set including a needle housing connected to a cannula housing. The needle housing has a pair of flexible sidewalls and a resilient band lockably engaged with the cannula. However, use of the Wojcik device is difficult due to angled insertion, and obtaining a desired fluid flow rate may require use of multiple devices. Mann discloses a similar device in U.S. Pat. No. 6,254,586. The Mann device is relatively complex and provides a needle in communication with a cannula in the body of a base. Mann uses a sensor mounted at a skin site and directly monitors fluid flow.

Kriesel, U.S. Pat. No. 5,858,005, discloses a device with similar fluid flow disadvantages, and is also relatively complex to manufacture. Livingston discloses a spring loaded subcutaneous injection set in U.S. Pat. No. 5,584,813. However, the Livingston device inserts a cannula into the subcutaneous layer, which may be undesirable. Further, the Livingston device also suffers from the same fluid flow disadvantages.

Van Antwerp discloses a subcutaneous injection set with a crimp-free soft cannula in U.S. Pat. No. 5,257,980. The Van Antwerp device inserts a cannula into the subcutaneous layer, and also has the same fluid flow limitations. Bartholomew discloses a subcutaneous injection set with improved cannula mounting arrangement in U.S. Pat. No. 5,176,662. The Bartholomew device has many of the same fluid flow disadvantages, and further includes a complex apparatus that inserts a cannula into the subcutaneous space. Quick discloses a needle device for use with subcutaneous catheter assemblies at U.S. Pat. No. 4,710,176. The Quick device comprises a needle inserted perpendicular to the skin, but has similar fluid flow limitations. Furthermore, the Quick device is relatively complex.

Kamen discloses a relatively simple infusion needle attachment in U.S. Pat. No. 4,380,234. However, the Kamen device maintains the fluid flow disadvantages, and is difficult to insert due to the angled approach. While not as simple as the Kamen device, Feller Jr. discloses an intravenous infusion assembly in U.S. Pat. No. 4,362,156. However, the Feller Jr. patent discloses an intravenous, rather than subcutaneous, device that is angularly delivered to the delivery site.

McFarlane discloses a relatively simple securing device for catheter placement assemblies in U.S. Pat. No. 4,129,128. The McFarlane device includes a catheter assembly, and two wings joined by a body that includes an arch configured to press a catheter into the skin surface.

It would be desirable therefore to provide an apparatus and method that overcomes these, and other, problems.

SUMMARY OF THE INVENTION

One embodiment of the invention provides a subcutaneous infusion device. The device includes a delivery tube including a central lumen, a closed first end and an open second end. The delivery tube is attached to a support base adjacent a first end of the delivery tube. A plurality of needles extend substantially perpendicular to the support base and in communication with the central lumen of the delivery tube.

Another embodiment of the invention provides a method for hydrating a patient. The method includes pressing a support base against a skin surface of the patient and inserting a plurality of needles into a subcutaneous skin layer responsive to the pressing. A saline fluid is delivered to the subcutaneous skin layer through the needles via a delivery tube.

Yet another embodiment of the invention provides a method for treating a skin ulcer. The method includes pressing a support base against a skin surface of the patient and inserting a plurality of needles into a subcutaneous skin layer responsive to the pressing. A saline fluid is delivered to the subcutaneous skin layer through the needles via a delivery tube.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The foregoing aspects and other attendant advantages of the present invention will become more readily appreciated by the detailed description taken in conjunction with the accompanying drawings.

BRIEF DESCRIPTION OF THE FIGURES

FIG. 1 illustrates a perspective view of one embodiment of a device used in accordance with the present invention;

FIG. 2 illustrates a side view of the device illustrated in FIG. 1 in a deployed position;

FIG. 3 illustrates a top view of the device illustrated in FIG. 1 in accordance with another aspect of the invention;

FIG. 4 illustrates a side view of a device comprising more than 2 needles, in accordance with another embodiment of the invention;

FIG. 5 illustrates a top view of a device comprising more than 2 needles, in accordance with another embodiment of the invention;

FIG. 8 illustrates a flowchart depicting one embodiment of a method for hydrating a patient in accordance with one embodiment of the invention.

DETAILED DESCRIPTION OF THE PRESENTLY PREFERRED EMBODIMENTS

Figure 6:
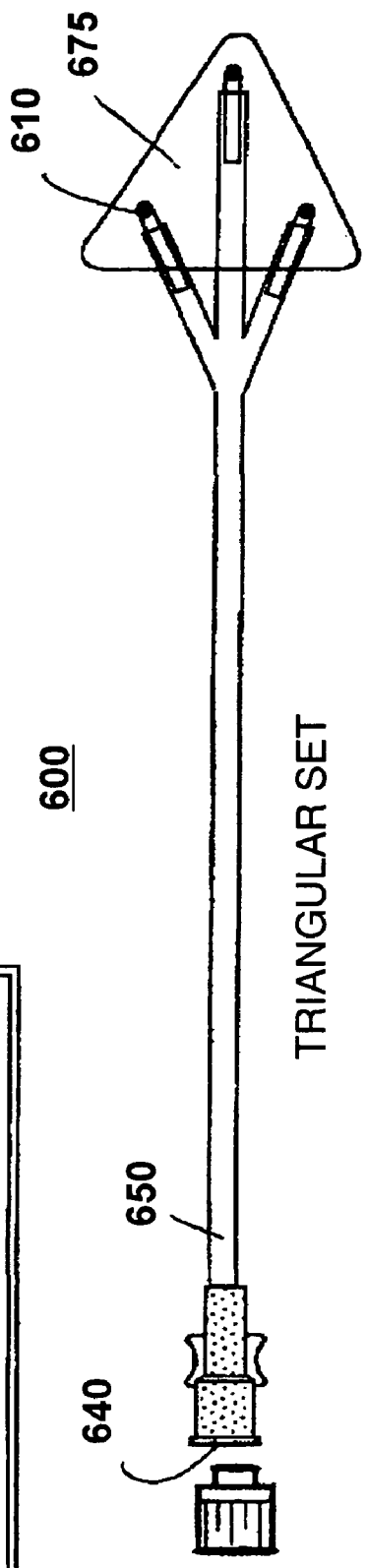
FIG. 6 illustrates a top view of a device comprising more than 2 needles, in accordance with another embodiment of the invention.

FIG. 1 illustrates a perspective view of a device for subcutaneous infusion of fluids in accordance with one aspect of the present invention. The device 100 includes a delivery tube 150, a support base 175, and a plurality of needles, 110, 120. The delivery tube includes a central lumen 105, a closed first end 130 and an open second end 140. Support base 175 includes an application side 136 and a side opposite 146 the application side.

Delivery tube 150, in one embodiment, is a cannula. In another embodiment, delivery tube 150 is a catheter. In another embodiment, delivery tube 150 is any biomedically suitable delivery tube configured to deliver fluid to a delivery site. In one embodiment, delivery tube 150 is affixed to an opposite side 146 opposite the application side 136. Lumen 105 is configured for fluidic communication with a fluid source (not shown) through the open first end 140. The delivery tube 150 may be fixedly attached 145 to the opposite side 146, or the delivery tube may be integral with the opposite side 146. In one embodiment, the delivery tube 150 is adhesively affixed to the opposite side 146.

Support base 175 is configured to provide support for the device 100 against a skin surface. FIG. 1 illustrates support base 175 configured in a generally rectangular shape. In another embodiment, support base 175 is configured to be substantially circular. In another embodiment, support base 175 is configured as a triangle or other polygon. In one embodiment, support base 175 comprises vinyl, although any biomedically suitable substance may be used. In one embodiment, the support base 175 is a flexible support, while in another embodiment, the support base 175 is substantially rigid. In another embodiment, support base 175 is substantially planar.

In one embodiment, the open second end 140 comprises a female luer fitting. In another embodiment, the luer fitting includes a luer fitting cap. The open second end 140 is configured to be connected to a fluid source (not shown), such as an IV bag, to supply fluid to the needles. In one embodiment, the fluid is a saline fluid. In another embodiment, the fluid is therapeutic and includes pharmaceutical compounds intended to have a beneficial therapeutic effect on a patient.

Needles 110 include a lumen 112. Lumen 112 is in fluidic communication with lumen 105 at a communication end 118 of the needle 110. Communication end 118 is disposed within the lumen 105. Needle 110 further includes a second open end disposed external to lumen 105. The second open end is configured to penetrate skin and deliver a fluid from the lumen 105 into the subcutaneous space. In one embodiment, the communication end 118 is flush with the inner surface of the lumen 105. In another embodiment, the communication end 118 is disposed within the lumen 105. In yet another embodiment, needle 110 is angled within the lumen 105 and the communication end 118 is disposed within the lumen 105.

Needles 110 may be sized based on treatment requirements. In one embodiment, needles 110 are 27 gauge needles, 6 millimeters long. In another embodiment, needles 110 are configured to provide a fluid flow rate of substantially 120 to 200 cc/hr. In another embodiment, needles 110 are configured to provide a flow rate of substantially 80 cc/hr.

In one embodiment, device 100 includes an adhesive 135 disposed upon the application side 136. The adhesive 135 is any appropriate, biomedically compatible adhesive. Adhesive 135 is disposed upon the entirety of the application side 136, in one embodiment. In another embodiment, adhesive 135 is disposed upon only a predetermined portion of the application side 136.

FIG. 1 further illustrates the device 100 adjacent a skin surface 195. Also illustrated is a subcutaneous skin layer 198.

FIG. 2 illustrates a side view of the device illustrated in FIG. 1 at 200. Like numbers in FIG. 2 illustrate like structures of FIG. 1.

FIG. 3 illustrates a side view of the device illustrated in FIG. 1 at 300. Like numbers in FIG. 3 illustrate like structures of FIG. 1.

FIG. 4 illustrates a side view of one embodiment of a device 400 in accordance with another aspect of the invention. The device 400 is similar to the device 100 and includes additional needles 410. Device 100 includes two needles 110, while device 400 includes 6 needles 410. It will be immediately apparent that a device in accordance with the invention can include any number of, but at least two, needles. Device 400 includes luer lock 440, delivery tube 450 and support base 475. In FIG. 4, needles 410 are configured in series.

FIG. 5 illustrates a top view of the device illustrated in FIG. 4 in accordance with one aspect of the invention.

FIG. 6 illustrates a device 600 for hydrating patients in accordance with another aspect of the invention. Device 600 includes a substantially triangular support base 675 and a plurality of needles 610. In the embodiment illustrated in FIG. 6, needles 610 are configured in parallel. In another embodiment, needles 610 are configured in series. Device 600 includes luer lock 640 and delivery tube 650 and other structures similar to the device 100.

Figure 7:
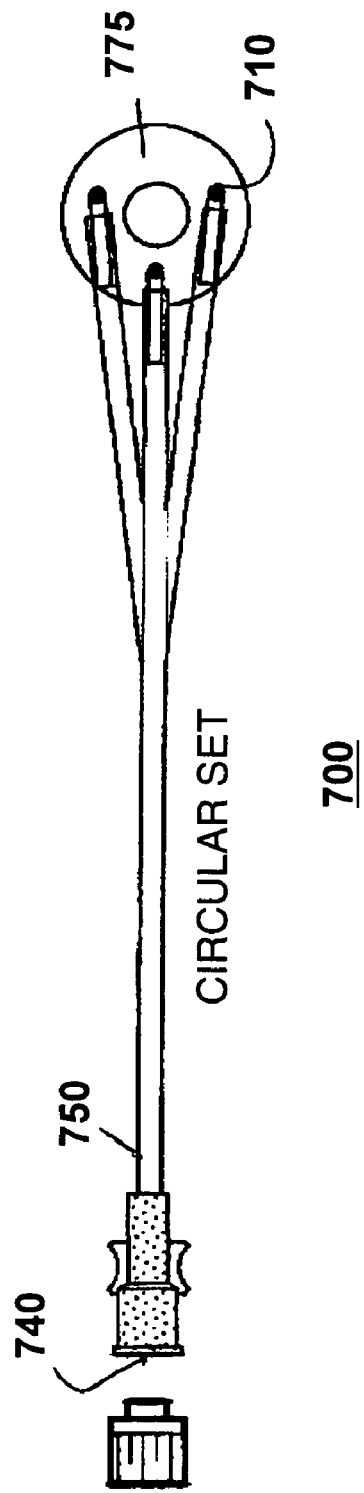
FIG. 7 illustrates a top view of a device comprising more than 2 needles, in accordance with another embodiment of the invention.

FIG. 7 illustrates a device 700 for hydrating patients in accordance with another aspect of the invention. Device 700 includes a substantially circular support base 775 and a plurality of needles 710. In the embodiment illustrated in FIG. 7, needles 710 are configured in parallel. In another embodiment, needles 710 are configured in series. Device 700 includes luer lock 740 and delivery tube 750 and other structures similar to the device 100.

FIG. 8 is a flowchart illustrating one embodiment of a method 800 for hydrating a patient in accordance with another embodiment of the invention. Method 800 begins at block 810 by pressing a support base against a skin surface of the patient. In one embodiment, the support base is a support base as illustrated in FIG. 1, 4, 6 or 7.

Method 800 continues at block 820 by inserting a plurality of needles into a subcutaneous skin layer responsive to the pressing. In one embodiment, the skin layer is in a fleshy area, such as, for example, an upper arm or thigh. In another embodiment, the skin layer is adjacent a skin ulcer.

Method 800 continues at block 830 by delivering a fluid to the subcutaneous skin layer through the needles via a delivery tube. In one embodiment, the fluid is a saline fluid. In another embodiment, the fluid is therapeutic and includes pharmaceutical compounds intended to have a beneficial therapeutic effect on a patient.

In this application, the terms "parallel" and "series" are ascribed a meaning similar to the meaning of those terms as applied in electronic circuits. Thus, needles configured in "parallel" have a common fluid source that divides to supply an individual needle, such as the embodiment illustrated in FIG. 6. Needles configured in series have a single fluid source for multiple needles, such as the embodiment illustrated in FIG. 4. Some embodiments of the invention may include needle configured in both series and parallel.

Practice of this invention allows for hydration of patients without intravenous approaches. Practice may also provide another method to treat skin ulcers by hydrating the skin surrounding the ulcer. Application of a growth hormone, or any other fluidic treatment regime, using the invention may be indicated under certain circumstances. Further, use of a plurality of needles in a single device allows for a greater variety of fluid flow levels.

Variations and alterations in the design, manufacture and use of the system and method are apparent to one skilled in the art, and may be made without departing from the spirit and scope of the present invention. While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A subcutaneous infusion device, comprising:
    a flexible delivery tube including a central lumen, a closed first end and an open second end, the flexible delivery tube including a plurality of needle openings;
    a flexible planar support base attached adjacent a first end of the delivery tube, the support base having a first side for supporting the flexible delivery tube and a second side; and
    a plurality of needles each needle having a first portion having a communication end, the first portion disposed within the central lumen of the flexible delivery tube and a second portion having an open end for penetrating skin and delivering fluid from the central lumen to a subcutaneous tissue, the second portion perpendicular to the first portion and extending through one of the plurality of needle openings and extending substantially perpendicular to the support base and in communication with the central lumen of the delivery tube;
    wherein the support base includes a plurality of openings, each of the plurality of openings for receiving one of the plurality of needles.

2. The device of claim 1 further comprising a luer fitting attached to the second end of the delivery tube.

3. The device of claim 1 wherein the needles are sized to allow a flow rate of approximately 120 to 200 cc/hr.

4. The device of claim 1 further comprising an adhesive disposed on at least a portion of the second side of the support base.

5. The device of claim 1 wherein a communication end of the needles extend into the central lumen of the delivery tube.

6. The device of claim 1 wherein at least two of the needles are configured in parallel.

7. The device of claim 6 wherein the flexible planar support base is circular having at least three openings for receiving at least three corresponding needles.

8. The device of claim 6 wherein the flexible planar support base is triangular having at least three openings for receiving at least three corresponding needles.

9. The device of claim 1 wherein the at least two of the needles are configured in series.

10. The device of claim 9 wherein the flexible planar support base is an elongated flexible base having at least six openings for receiving six needles.

11. A subcutaneous infusion device, comprising:
    a flexible delivery tube including a central lumen, a closed first end and an open second end, the flexible delivery tube including a plurality of needle openings;
    a rigid planar support base attached adjacent a first end of the delivery tube, the support base having a first side for supporting the flexible delivery tube and a second side positioned opposite the first side; and
    a plurality of needles each needle having a first portion having a communication end, the first portion disposed within the central lumen of the flexible delivery tube and a second portion having an open end for penetrating skin and delivering fluid from the central lumen to a subcutaneous tissue, the second portion perpendicular to the first portion and extending through one of the plurality of needle openings and extending substantially perpendicular to the support base and in communication with the central lumen of the delivery tube;
    wherein the support base includes a plurality of openings aligned with the plurality of needle openings of the flexible delivery tube each of the plurality of openings for receiving one of the plurality of needles and wherein the second side includes an adhesive layer for removably attaching the support base to a patient's skin.

12. The device of claim 11 further comprising a luer fitting attached to the second end of the delivery tube.

13. The device of claim 11 wherein the needles are sized to allow a flow rate of approximately 120to 200 cc/hr.

14. The device of claim 11 further comprising an adhesive disposed on at least a portion of the second side of the support base.

15. The device of claim 11 wherein a communication end of the needles extend into the central lumen of the delivery tube.

16. The device of claim 11 wherein at least two of the needles are configured in parallel.

17. The device of claim 16 wherein the rigid planar support base is circular having at least three openings for receiving at least three corresponding needles.

18. The device of claim 16 wherein the rigid planar support base is triangular having at least three openings for receiving at least three corresponding needles.

19. The device of claim 11 wherein the at least two of the needles are configured in series.

20. The device of claim 11 wherein the rigid planar support base is an elongated rigid base having at least four openings each for receiving one of four needles.

* * * * *